United States Patent [19]

Yamazoe et al.

[11] Patent Number: 4,843,247

[45] Date of Patent: Jun. 27, 1989

[54] DETERMINATION OF ASPHALTENE CONTENT AND DEVICE THEREFOR

[75] Inventors: Seigo Yamazoe; Hiroshi Tsuji, both of Saitama, Japan

[73] Assignee: Cosmo Oil Co., Ltd., Tokyo, Japan

[21] Appl. No.: 80,511

[22] PCT Filed: Nov. 7, 1986

[86] PCT No.: PCT/JP86/00565
§ 371 Date: Jul. 8, 1987
§ 102(e) Date: Jul. 8, 1987

[87] PCT Pub. No.: WO87/03090
PCT Pub. Date: May 21, 1987

[30] Foreign Application Priority Data

Nov. 8, 1985 [JP] Japan ................... 60-248733

[51] Int. Cl.$^4$ ............................................. G01N 15/06
[52] U.S. Cl. ................................. 250/573; 356/436
[58] Field of Search ............... 250/226, 573; 356/436, 356/437, 440

[56] References Cited

U.S. PATENT DOCUMENTS

| 2,761,067 | 8/1956 | Troy, Jr. | 250/573 |
| 3,790,156 | 6/1975 | Heigl et al. | 356/440 |
| 4,136,959 | 1/1979 | Honkawa et al. | 356/436 |
| 4,544,840 | 10/1985 | Keller | 250/573 |

Primary Examiner—David C. Nelms
Attorney, Agent, or Firm—Sughrue, Mion, Zinn, Macpeak & Seas

[57] ABSTRACT

A method for precisely and effectively determining an asphaltene content in a heavy hydrocarbon oil which can be applicable to a wider range of asphaltene content is disclosed. The method comprises measuring absorbances of a sample solution having dispersed therein asphaltene particles at two different wavelengths being at a distance of at least 50 nm selected from the visible light range of from 500 to 1,000 nm and obtaining an asphaltene content from the two measured values utilizing a relationship. A device is also disclosed for determining asphaltene content in a sample solution. It includes dipping a means for determining the absorbances at two different wavelengths into each probes which are in a line, or connecting the means into a flow cell and passing the sample solution through the flow cell to determine the absorbances.

7 Claims, 2 Drawing Sheets

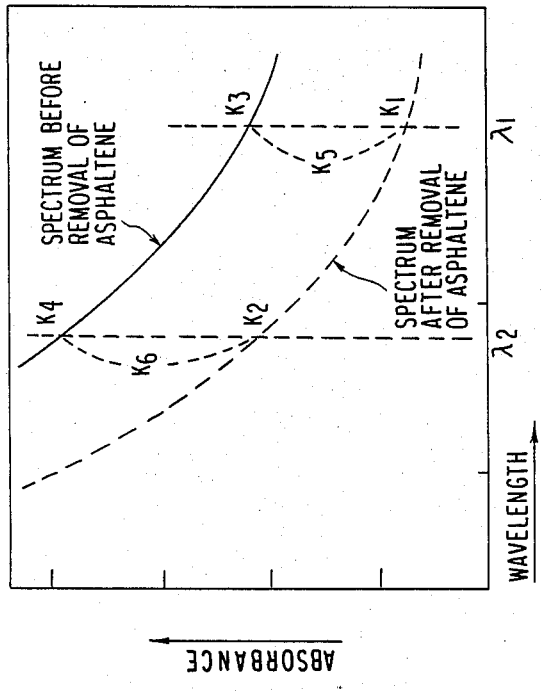

| SAMPLE OIL | ASPHALTENE CONTENT (A) BY INVENTION (WT %) | PRECISION OF REPRODUCIBILITY (COEFFICIENT OF VARIATION) (%) | CONVERTED FROM (A) (WT%) | | FOUND CONTENT (WT%) | |
|---|---|---|---|---|---|---|
| | | | ASPHALTENE CONTENT BY IP-METHOD | ASPHALTENE CONTENT BY UOP-METHOD | ASPHALTENE CONTENT BY IP-METHOD | ASPHALTENE CONTENT BY UOP-METHOD |
| SHALE OIL OF FUSHUN, CHINA | 1.2 | 3.60 | 0.79 | 1.0 | 0.78 | 1.0 |
| C HEAVY FUEL OIL | 5.5 | 1.31 | 3.8 | 4.7 | 3.7 | 4.8 |
| IRANIAN HEAVY SHORT RESIDUE | 12.8 | 4.80 | 8.8 | 10.9 | 9.1 | 10.6 |
| ARABIAN HEAVY SHORT RESIDUE | 17.9 | 4.75 | 12.3 | 15.3 | 13.1 | 15.7 |
| TAR SAND OIL (COLD BREAK) | 24.5 | 4.67 | 16.8 | 20.9 | 16.0 | 21.3 |
| THERMALLY CRACKED OIL | 29.5 | 2.65 | 20.2 | 25.0 | 21.4 | 25.9 |

DETERMINATION OF ASPHALTENE CONTENT AND DEVICE THEREFOR

TECHNICAL FIELD

This invention relates to a method of rapid determination of asphaltene content in heavy hydrocarbon oils, such as long residue, short residue, hydrocracked oil, thermally cracked oil, shale oil, tar sand oil, etc., and to a device for automatically carrying out such determination.

BACKGROUND ART

An asphaltene content in heavy hydrocarbon oils is not only an indication of combustibility and storage stability of heavy hydrocarbon oils but also an important factor greatly influencing catalytic activity in a direct disulfurization process. Therefore, it is required to carry out determination of asphaltene content in heavy hydrocarbon oils rapidly and precisely from consideration of product control and process control.

Determination of asphaltene content has been commonly carried out based on a method of The Institute of Petroleum (IP 143, hereinafter referred to as IP method). IP method comprises dissolving a sample in a prescribed amount of warm n-heptane, filtering the resulting mixture using a filter paper, washing an insoluble matter collected by filtration with heptane at reflux in a Soxhlet's extractor, extracting the insoluble matter with toluene in the extractor, and determining the extracted soluble matter. However, since the IP method involves complicated operations and requires much time as long as 9 hours for analysis, it has been partly replaced by a method of Universal Oil Product Co. (UOP 614/80, hereinafter referred to as UOP method), in which a sample dissolved in a prescribed amount of warm n-heptane is filtered through a membrane filter and the insoluble matter collected on the filter is determined as an asphaltene content. The UOP method, however, still requires about 4 hours for analysis, and the measured values do not agree with those obtained by IP method. Accordingly, it has been demanded to develop a simple and rapid method of asphaltene determination which gives measured values in good agreement with IP values.

Methods of rapid determination of asphaltene content so far proposed include (1) Ono method (Tastuo Ono, *J. of Japan Petrol. Inst.*, Vol. 14, No. 9, 504 (1971)), (2) absorptiometric methods (Tsutomu Kaibara et al., *J. of Japan Petrol. Inst.*, Vol. 23, No. 3, 178 (1980)), and (3) hydrogen flame ionization detection thin-layer chromatographic methods (FID-TLC) (Marc-Andre Poirier et al., *J. of Chromatographic Science*, Vol. 21, No. 7,331 (1983) and Yojiro Yamamotlo et al., *J. of Japan Petrol. Inst.*, Vol. 27, No. 3,269 (1984)).

The Ono method comprises the same procedures as IP method except for omitting the toluene extraction, and the time required for analysis and measured values are substantially equal to those of the UOP method.

The hydrogen flame ionization detection thin-layer chromatographic method by Yamamoto et al. comprises spotting a sample solution on a silica gel thin layer rod, developing the sample with a solvent, e.g., toluene, to separate asphaltene, and determining the asphaltene content by means of a flame ionization detector. Although this method succeeded to furnish measured values in correlation with IP values and to reduce the time required for analysis to 30 to 60 minutes per 10 samples, it has disadvantages in that an analyst should always scan the system throughout measurement and that analysis precision greatly depends on development conditions, resulting in poor reproducibility.

The absorptiometric method by Kaibara et al. comprises dissolving a sample in n-heptane, measuring absorbance of the solution at a wavelength of 700 nm by means of a spectrophotometer, further measuring absorbance of a filtrate obtained by filtration of the solution at a wavelength of 700 nm, and obtaining an asphaltene concentration from a difference in absorbance of the solution between before and after the filtration. According to this method, the time required for analysis is reduced to about 30 minutes. However, the operation of filtration is complicated, and the measured values, though correlating with IP values, has a coefficient of correlation of 0.979, that is lower than a generally acceptable coefficient of correlation, i.e., not less than 0.99.

Another problem is that the upper limit of determination range is 3% by the conventional methods. Incidentally, an asphaltene content in heavy hydrocarbon oils, which depends on a kind of crude oil and cut fraction, is generally 1 to 5% in long residue and 5 to 30% in short residue. In addition, tar sand oil contains such a large amount of asphaltene content as 15 to 20%. In Japan, a research and development relating to techniques for lightening a heavy hydrocarbon oil has widely advanced from a view point of recent oil supplying circumstances. Thus, it has been desired to provide a method for rapid determination of asphaltene content as wide as possible.

A method and device of the present invention is developed to resolve various problems of the conventional asphaltene content determination means. The method of the present invention can determine asphaltene content at a wider range concentration and more rapidly as compared with the conventional methods by combining a means of sample preparation for precipitation of asphaltene and a method for two-wavelength absorbance detection connected thereto. The device of the present invention provide a determination device composed of a two-wavelength absorbance detector to determine asphaltene content by the afore-mentioned means, an automatic sample feeder connected thereto, and a microcomputer and make it possible asphaltene determination by which a number of samples can be analyzed surely and rapidly without requiring much labor.

DISCLOSURE OF INVENTION

A basic technique of the determination method according to the present invention is as follows.

(1) An appropriate amount (G) of a sample oil is weighed, and a prescribed amount of a solvent is added thereto, followed by stirring. The solution is then placed under prescribed conditions hereinafter described so as to provide and precipitate asphaltene particles in particle size distribution as narrow as possible to prepare a sample solution having dispersed therein the asphaltene particles. Light is transmitted through the solution in a dispersion condition without removing the asphaltene particles, and optical densities (hereinafter referred to as absorbance(s)) of the sample solution at two different wavelengths, which are appropriately aparted from each other within a visible light range of from 500 to 1,000 nm. The visible absorption spectrum of the above-described sample solution having dispersed therein asphaltene particles in the visible light region of from 500 to 1,000 nm does not have its maximum and shows a tendency of substantially linear drop in accordance as the wavelength becomes longer. FIG. 1 illustrates the principle of the determination method according to the present invention, in which the x axis of abscissa indicates a wavelength of light (nm) and the y axis of ordinate indicates an absorption spectrum of the above-described sample solution and the solution (named as "blank") having been removed the asphaltene particles from the above-described solution by any means, such as filtration. In FIG. 1, the solid line is the absorption spectrum of the sample solution before removal of asphaltene, while the dotted line is an absorption spectrum of the sample solution after removal of asphaltene.

Since the asphaltene particles do not substantially transmit light in a wavelength region of from 500 to 1,000 nm, the absorbance of a sample solution from which the asphaltene particles have been removed by any means, such as filtration, is uniformly lower than that of a sample solution before asphaltene removal in proportion to the asphaltene concentration. More specifically, it has been confirmed through investigations on various heavy hydrocarbon oils that there is a first-order correlation between a ratio of (a difference between absorbance $K_4$ of the sample solution before removal of asphaltene particles at wavelength $\lambda_2$ and absorbance $K_3$ of the same solution at wavelength $\lambda_1$) to absorbance $K_3$, i.e., $(K_4 - K_3) \times 100/K_3$, (hereinafter referred to as rate of increase) and a ratio of absorbance $K_1$ of the sample solution after removal of asphaltene particles at wavelength $\lambda_1$ to absorbance $K_3$, i.e., $K_1 \times 100/K_3$, (hereinafter referred to as blank rate) even if the kind or asphaltene content of oil changes.

Therefore, absorbance $K_1$ of a maltene (soluble matter) at analytical wavelength of light can be obtained by measuring absorbances of a sample solution as having dispersed therein asphaltene particles at two different wavelengths appropriately selected and inserting the measured values in the correlation of rate of increase with blank rate. Further, absorbance $K_5$ of the asphaltene particles can be obtained from a difference between $K_3$ and $K_1$.

Thus, once a calibration curve is prepared from a standard asphaltene, which is preferably prepared in accordance with IP method, a weight of asphaltene (g) corresponding to absorbance $K_5$ is first obtained from the calibration curve, and an asphaltene content of a sample oil is then obtained through equation:

Asphaltene content = $g \times 100/G$(wt %)

(2) The asphaltene content may also be obtained by using one calibration curve from absorbances $K_3$ and $K_4$. In this case, such a calibration curve is based on a first-order correlation between an absorbance ratio $K_4/K_3$ and a ratio of gram of asphaltene (g) in a sample solution to absorbance $K_3$, $g/K_3$. The asphaltene gram in the sample solution can be obtained in the same manner as described above (e.g., by using a centrifugal separation technique).

Accordingly, if a relationship between the ratio $K_4/K_3$ and the ratio $g/K_3$ for a known sample is once established, subsequent asphaltene determinations can be effected simply by measuring absorbances $K_3$ and $K_4$, obtaining an asphaltene weight g from a previously prepared calibration curve, and calculating an asphaltene content from the equation:

Asphaltene Content = $g \times 100/G$(wt %)

(3) In accordance with the above-described method of determination, determined values of about 50 kinds of heavy hydrocarbon oils having asphaltene contents between 0.1 to 30% by weight correlate with IP and UOP values with a coefficient of correlation of 0.99 or more and, in addition, with a coefficient of variation of 5% or less, which indicates excellent analytical precision as compared with IP method having a coefficient of variation of 10% or less. Time required for a cycle of analysis is about 40 minutes. However, since a large number of samples may be subjected to analysis all at once, the requisite time per sample is markedly reduced when compared with conventionally proposed rapoid determination methods. For example, when ten samples are analyzed all at once, the requisite time per sample is 10 minutes at the longest.

The method and device of the present invention is to realize the above-described processes. They are composed of the following element of the invention:

1. A method for determining an asphaltene content in a heavy hydrocarbon oil, which comprises measuring absorbances of a sample solution having dispersed therein asphaltene particles which is prepared from a sample oil to be determined at two wavelengths selected from a visible light region of from 500 to 1,000 nm, inserting the measured values into a relationship between known asphaltene contents and absorbances at two wavelengths, and performing an operation.

2. A method for determining an asphaltene content in a heavy hydrocarbon oil as in the above Item 1, wherein the sample solution is prepared by adding an aromatic hydrocarbon to a sample oil to dissolve in each other, adding a warm aliphatic hydrocarbon to the solution to precipitate asphaltene particles, and cooling the solution or allowing the solution to cool.

3. A method for determining an asphaltene content in a heavy hydrocarbon oil as in the above Items 1 or 2, wherein the two wavelengths selected for absorbance measurement are at least 50 nm apart.

4. A device for determining an asphaltene content in a heavy hydrocarbon oil, which comprises a dip probe or flow cell for sampling a sample solution having dispersed therein asphaltene particles which is prepared from a sample oil to be determined, said dip prove or flow cell being set so as to face with the sample solution and being movable with up-and-down strokes so as to be in contact with or apart from the sample solution, a two-wavelength absorbance detector including a light source, passages for light to allow the light from the light source to pass through a sample solution of a given thickness introduced in the dip probe or flow cell, two interference filters each capable of transmitting the light having transmitted through the sample solution having a different wavelength selected from a range of from 500 to 1,000 nm, and phototubes or photocells each capable of converting the intensity of each of incident light and transmitted light having two different wavelengths into an electrical current, and a computing means capable of converting the electrical current values into an asphaltene content.

5. A device for determining an asphaltene content in a heavy hydrocarbon oil as in the above Item 4, wherein the two wavelengths selected for absorbance measurement are at least 50 nm apart.

6. A device for determining an asphaltene content in a heavy hydrocarbon oil as in the above Items 4 or 5, wherein the dip probe or flow cell is provided with a washing means for removing the sample solution for determination attached to or remained on the dip probe or flow cell by passing a washing solution every time absorbances of the sample are determined.

7. A device for determining an asphaltene content in a heavy hydrocarbon oil as in the above Items 4 to 6, wherein said device further includes a means for controlling the washing means, every time the determination of one sample is completed, provided to the dip probe or flow cell with the successive determination of each absorbances of the sample contained the sample containers by moving with the dip probe or flow cell.

BRIEF EXPLANATION OF THE DRAWINGS

FIG. 1 is a spectrum line of an absorbance of transmitted light with respect to a sample solution and a sample solution having been filtered in a visible region.

FIG. 2 is a synoptical drawing to determinate asphaltene contents in heavy hydrocarbon oil.

BEST MODE FOR CARRYING OUT THE INVENTION

(1) Method for Determination

Figure 3:
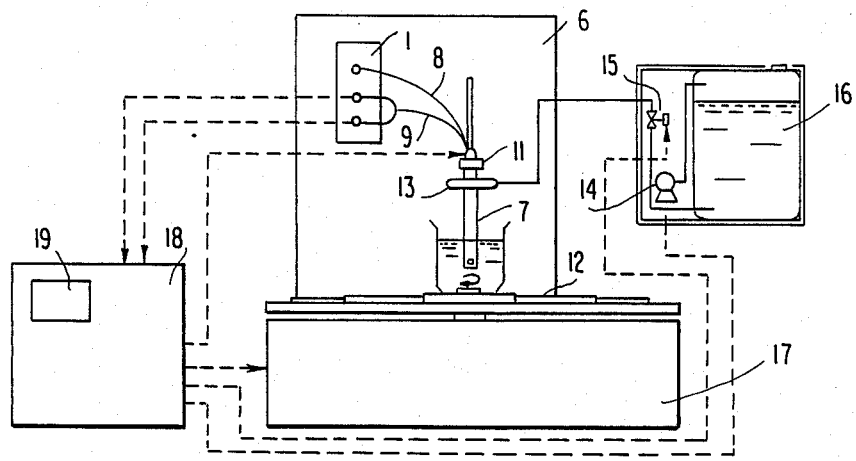
FIG. 3 is a schematic view of the automatic determination device according to a dip probe system used in an example of the present invention.

In the preparation of a sample solution to be analyzed, asphaltene particles present in a sample oil can be precipitated as fine particles with a narrow size distribution by following specific procedures hereinafter described. The particle size and its distribution of precipitated asphaltene particles have great influences upon the measurable range of asphaltene contents and precision of measurements in the subsequent two-wavelength absorptiometry. The sample solution should be stirred throughout the measurement so as to prevent sedimentation of asphaltene particles in the solution thereby to stably maintain the state of uniform dispersion. Light from a light source is led by optical fibers to the sample solution as incident light and then transmitted through the solution having a given thickness. Absorbances (optical densities) of the sample solution at two different wavelengths within a range of from 500 to 1,000 nm are measured.

Intensity of each of the two transmitted light rays having different wavelengths is converted into an electrical current value by means of a light-current transducer, which is then put into a computer having a prescribed program thereby to print out an asphaltene content in the sample oil.

The above-mentioned two-wavelength absorbance detection can be carried out by either a dip probe system or a flow cell system. In the former system, a dip probe quipped with an opening and a reflector at the end is dipped in a sample solution, and incident light and transmitted light are led through optical fibers incorporated in the probe. In the latter system, a sample solution is introduced by suction in a flow cell, with optical fibers for leading incident light and those for leading transmitted light being fixed on opposite sides of the flow cell. In either case, once a plurality of different sample solutions are prepared in advance, asphaltene contents of sample oils can be determined efficiently in a successive manner. It should be noted, however, that it is necessary to wash the dip probe or flow cell with a washing solvent after every measurement to remove any remaining sample solution attached thereto.

The above-described operation can be controlled under a computer program at a great saving of labor.

The process for preparing samples which can be analyzed in the present invention comprises placing an appropriate amount (e.g., from 0.3 to 5.0 g) of a sample oil in a beaker having a prescribed volume (e.g., 100 ml), adding a small amount (e.g., from 0.3 to 5.0 ml, and preferably 1.0 ml) of an aromatic hydrocarbon solvent (e.g., toluene) to the beaker to dissolve the content, further adding a prescribed amount (e.g., 100 ml) of an aliphatic hydrocarbon solvent (e.g., n-heptane) to the solution while stirring to precipitate asphaltene. The aliphatic hydrocarbon solvent used above may be heated to a temperature of from about 40° to about 90° C., and preferably 80° C.

Then, the contents of the beaker is allowed to cool at room temperature, preferably at a temperature of from 15° to 30° C., for about 30 minutes to prepare the samples of the present invention. The aromatic hydrocarbon solvent to be used includes benzene, toluene, and xylene. The aliphatic hydrocarbon solvent to be used includes those having from 5 to 12 carbon atoms, such as pentane, hexane, heptane, octane, etc.

In order to ensure dispersion stability of the asphaltene particles by preventing a tendency of sedimentation, the sample solution may further contain a surface active agent, a dispersant for engine oil, etc.

By the above-described process of preparing a sample solution, asphaltene particles having a narrow size distribution between about 1 $\mu$m and 3 $\mu$m can be formed, which brings about great effects to widen the range of measurable asphaltene contents and increase precision in the subsequent two-wavelength absorbance detection.

The thus prepared sample solution having dispersed therein the asphaltene particles without removing the asphaltene content is subjected to absorbance measurement, while being stirred by means of a magnetic stirrer, and the like, at two wavelengths being at a distance of at least about 50 nm, and preferably from 50 to 150 nm, for example, at an analytical wavelength of 800 nm and at a control wavelength of 675 nm. If the distance between the two wavelengths is less than 50 nm, determination precision becomes poor.

Referring to FIG. 1, when the absorbance of a sample solution at an analytical wavelength of 800 nm ($K_3$) and that at a control wavelength of 675 nm ($K_4$) are found to be 1.10 and 1.98, respectively, then the equation for rate of increase gives $(K_4-K_3)\times 100/K_3=80.0$ From the correlation between rate of increase and blank rate, one may obtain a blank rate of 29.1. It follows that $K_1$ (absorbance of a maltene after removal of asphaltene at 800 nm)=0.32. Therefore, $K_3-K_1$ (absorbance of asphaltene)=$K_5$=0.78. The weight of asphaltene can be obtained from a calibration curve of absorbance $K_5$ and asphaltene weight g. From this value, the asphaltene content in the sample oil can be obtained.

FIG. 2 shows results of determinations for asphaltene content in heavy hydrocarbon oils in accordance with the dip probe system of the present invention, which comprises the process for preparing sample solutions for determination of light intensity to which a small of aromatic hydrocarbon is added and the two-wavelength absorbance detection method, in comparison with values of the same hydrocarbon oils obtained by conventionally known determination methods. It can be seen from FIG. 2 that the method and device in accordance with the present invention make it possible to determine a wide range of asphaltene contents at high precision of analysis.

The measured values given in FIG. 2 were computed in accordance with the second method of calculation using the relationship between $K_4/K_3$ and $g/K_3$. In this particular case, there is established an equation:

*Asphaltene Content (wt %)* $= 0.0287 \times (2.43\ K_3 - K_4) \times 100/G$

The coefficient of variation in FIG. 2 was calculated for 6 measurements from equation:

*Coefficient of Variation (%)* $=$ *(Standard Deviation expressed in Square Root of Unbiased Variance)* $\times 100/Mean$ When determinations are carried out on the same samples as used in FIG. 2 by a flow cell system according to the present invention, the results obtained are almost equal to those of FIG. 2.

(2) Device for Determination (i). Dip Probe System

When a container containing a stirrer of a magnetic stirrer and a sample solution is carried to a predetermined position where the sample solution and a dip probe face to each other (location of measurement), the magnetic stirrer is caused to rotate to agitate the sample solution and, at the same time, the probe and/or the container goes up or down whereby the end of the probe, i.e., the measurement part, is dipped in the sample solution to a depth necessary and sufficient for absorbance measurement.

The dip probe contains therein optical fiber bundles leading incident light and transmitted light, respectively. Light having transmitted through the sample solution is passed through two interference filters differing in wavelength that are placed in parallel at the outlet of the optical fiber bundle for transmitted light, where optical densities (absorbances) of the sample solution are determined at two different wavelengths falling within a range of from 500 to 1,000 nm.

The intensity of the light having transmitted through each filter is converted into electrical current by a light-current transducer, such as a phototube, a photocell, etc., and the resulting current value is introduced into a computer having a specified program to perform an operation to print out the asphaltene content in the sample oil.

Upon completion of asphaltene determination, the dip probe and the container are separated from each other under instructions from the computer, and an electromagnetic valve of a washing means is opened also on instructions of the computer thereby to jet a washing solvent fed from the washing means against the probe to wash away any sample solution attached to the measurement part of the probe. The washing solvent is introduced in the container containing the sample solution having been analyzed. After thorough washing of the probe, the electromagnetic valve is closed to stop washing, and the container is removed from the location of measurement, while a container containing another sample solution and a magnetic stirrer is successively placed on the location of measurement.

Through these procedures, one cycle of asphaltene determination is completed.

Figure 4:
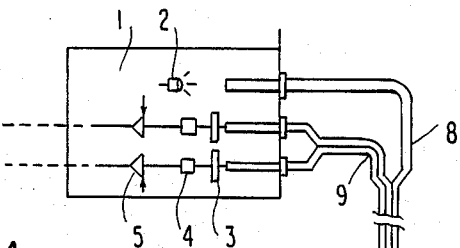
FIG. 4 is an enlarged view of the two-wavelength absorbance detector used in the device of FIG. 3.

FIGS. 3 and 4 shows schematic views of a divice which can be used for performing dip probe system asphaltene determination. FIG. 4 represents an enlarged view of the dominant part of FIG. 3. In these figures, two-wavelength absorbance detector 1 is composed of a photometry part comprising light source 2 (e.g., a tungsten lamp), interference filters 3 (e.g., 675 nm and 800 nm), phototube (or solar cell) 4, and amplifier 5 and a measurement part (i.e., dip probe 7) contained in elevator 6, both parts being connected to each other via optical fiber bundle 8 for incident light and optical fiber bundles 9 for transmitted light. For details of the photometry part FIG. 4 can be referred to. Dip probe 7 has an opening (e.g., 3 mm in height and 8 mm in width) and reflector 10 at the lower end and is held by holder 11 of elevator 6 (shown in FIG. 3). Probe 7 goes down to enter in a sample solution on measurement and goes up to stand apart from the sample solution during washing and rotation of turn table 12.

By reference to FIG. 3, elelvator 6 is equipped with nozzles 13 for washing the dip probe that are aligned in a ring around the probe and connected to washing solvent-containing tank 16 equipped with miniature compressor 14 and electromagnetic valve 15 via a Teflon tube. Elelvator 6 is fixed to automatic sample feeder 17 having turn table 12 (e.g., setting 12 beakers) and a magnetic stirrer at the location of measurement. Starting and stopping of elevator 6, miniature compressor 14, and turn table 12, and opening and closing of electromagnetic valve 15 are all controlled under instructions from microcomputer 18. The current output from two-wavelength absorbance detector 1 is introduced in the microcomputer, where the current is converted into an asphaltene content which is then printed out by printer 19.

More specifically, the magnetic stirrer of automatic sample feeder 17 starts to rotate at a signal from microcomputer 18 to agitate a sample solution in a beaker set on a location of measurement. At the same time, elevator 6 starts to let probe holder 11 down so that the opening of the probe may be dipped in the sample solution. Visible light rays emitted from light source 2 of two-wavelength absorbance detector 1 pass through optical fibers 8 for incident light to reach the dip probe and transmit through the sample solution from the opening. The light is partly absorbed in the sample solution and partly reflectled on reflector 10. The reflected light is again absorbed in the sample solution and passes through optical fibers 9 for transmitted light to reach interference filters 3, where transmitted light rays having two wavelengths are chosen by two interference filters 3 and each is converted into elecrical current by respective phototube 4, amplified by respective amplifier 5, and then introduced in microcomputer 18.

In microcomputer 18, the current input is converted into transmittance T (ratio of transmitted light I/incident light $I_0$), which is then converted into absorbance K ($\log_{10} 1/T$). The resulting absorbance values are applied to a correlation of rate of increase-blank rate and a calibration curve of absorbance difference $K_3-K_1$ vs. asphaltene content that have previously been put in the computer to calculate an asphaltene content, which is then put in printer 19. At the same time, the thus obtained asphaltene content is converted into an IP asphaltene content and an UOP asphaltene content by using a previously incorporated correlationships between asphaltene content of the invention and that of IP method and between asphaltene content of the invention and that of UOP method. Upon completion of input, signals are issued from microcomputer 18 to start miniature compressor 14, whereby the inner pressure of tank 16 is increased. Subsequently, elevator 6 starts to move, and as probe holder 11 goes up, electromagnetic valve 15 is opened to let a washing solvent (e.g., n-heptane) spout from nozzles 13 to clean dip probe 7.

Then, turn table 12 of automatic sample feeder 17 again starts to move to set the next sample solution to be analyzed on the location of measurement, and the same operations as described above are automatically repeated.

In the case where measurements are made on samples that are not easily washed off by jetting a solvent from nozzles, cleaning effects may be assured by feeding a sample solution-containing beaker and a beaker containing a washing solvent (e.g., toluene) alternatingly on the turn table 12.

(ii). Flow Cell System

A flow cell system device wherein a flow cell is used in place of the dip probe works in the same manner as described for the dip probe system device except that the ends of optical fiber bundles guiding incident light and transmitted light, respectively, are fixed to both sides of transparent flow cell so as to face to each other and that the washing means as used in the dip probe system is replaced with a pumping means to withdraw a sample solution having been analyzed.

According to the flow cell system, when the end of a suction pipe connected to a flow cell is dipped in a sample solution, the sample solution is introduced in the suction pipe by the action of a vacuum pump and then made to flow in the flow cell. Absorbances of the sample solution are measured while the solution stream passes between two ends of optical fiber bundles guiding incident light and transmitted light, respectively. The sample solution is then withdrawn into an enclosed waste liquor reservoir. The waste liquor reservoir is evacuated by removing air with a vacuum pump so as to permit the next sample solution be sucked into a suction pipe at a predetermined flow rate. The evacuation is conducted via a cold trap so as to prevent contamination of the pump due to the waste liquor and gas. After every determination, any remaining sample solution attached to the suction pipe, flow cell, etc. can be washed away by replacing the beaker containing the sample solution with a container containing a washing solvent. Therefore, the flow cell system eliminates the need of an independent washing means as required in the dip probe system.

Other operations are almost same as described in the above Item (i).

Figure 5:
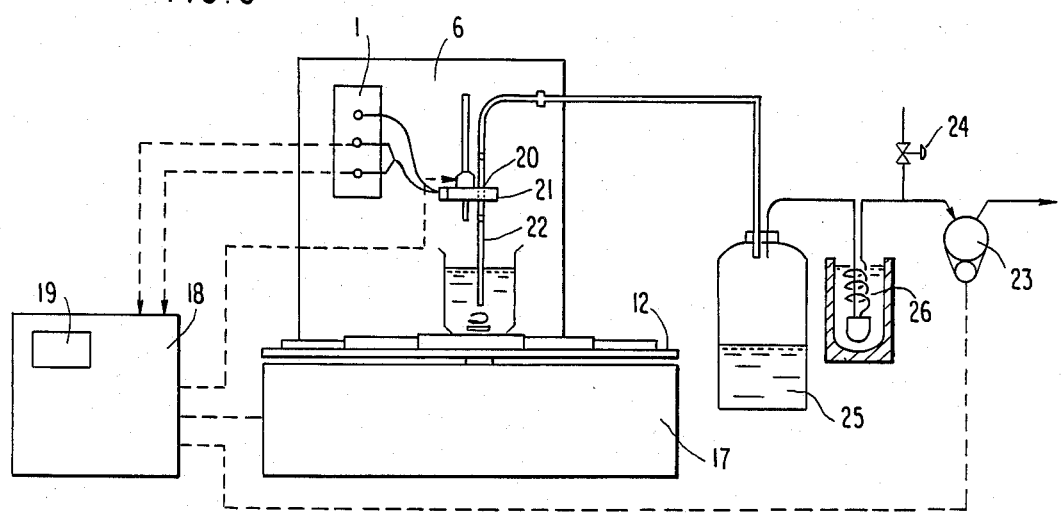
FIG. 5 is a schematic view of the automatic determination device according to a flow cell system used in an example of the present invention.

FIG. 5 illustrates a schematic view of a device for determining asphaltene contents according to the flow cell system. Elevator 6 starts to move at a signal from microcomputer 18, whereby flow cell 20 (e.g., a glass-made cell having a thickness of 3 mm) held by flow cell holder 21 goes down until the end of suction pipe 22 (e.g., a Teflon pipe having an inner diameter of 2 mm) connected to the lower end of flow cell 20 reaches a sample solution while being stirred with a magnetic stirrer, which is set on automatic sample feeder 17 at a location of measurement. Vacuum pump 23 is then started to suck the sample solution at a certain flow rate (preferably from 10 to 30 ml/min) due to reduced pressure appropriately adjusted by means of pressure control valve 24. While the sample solution passed through flow cell 20, light having transmitted through the sample solution at two wavelengths (e.g., 675 nm and 800 nm) is detected by two-wavelength absorbance detector 1, where measured intensities of transmitted light are converted into electrical current values. The resulting current outputs are inserted in microcomputer 18, where they are converted into absorbances. The input of current values in microcomputer 18 is preferably conducted after about 20 seconds from the state of vacuum pump 23.

Upon completion of one cycle of determination, elevator 6 goes up to lift suction pipe 22 and, after several seconds, vacuum pump 23 is stopped. The driving time of vacuum pump is preferably about 60 seconds. Then, automatic sample feeder 17 starts to cause turn table 12 to rotate, whereby a beaker containing a washing solvent (e.g., toluene) is set on the location of measurement, followed by suction of the solvent with vacuum pump 23 to wash the inner walls of suction pipe 22 and flow cell 20. After completion of washing, turn table 12 again rotates to carry the next sample solution to the location of measurement.

A series of the aforesaid operations is all controlled by programmed microcomputer 18. The results of asphaltene determination are successively printed out by printer 19 upon giving instructions to computer 18.

The sample solution having been analyzed and the washing solvent are collected in waste liquor reservoir 25. In order to prevent contamination of vacuum pump 23, it is preferable to insert cold trap 26 between reservoir 25 and pump 23.

In FIG. 5, flow cell holder 21 to which flow cell 20 is fixed and two-wavelength absorbance detector 1 are connected to elevator 6. Flow cell 20 and holder therefor 21 may be fitted at any position of the pipeline in which a sample solution fed from suction pipe 22 flows and should not be necessarily fixed to elevator 6. Two-wavelength absorbance detector 1 also should not be necessarily fixed to elevator 6. What is required is that the end of suction pipe 22 moves with up-and-down strokes so as to be dipped in a sample solution and then lifted. Therefofe, in cases where flow cell holder 21 is not fixed to elevator 6, suction pipe 22 may be fixed to elevator 6 at a site near to the end thereof.

INDUSTRIAL APPLICABILITY

As described above, the present invention eliminates disadvantages associated with the conventional methods of determining asphaltene contents in heavy hydrocarbon oils, such as time requirement per sample, complicated operations, labor requirement, narrow ranges of measurement, unsatisfactory precision in some cases, and the like. In other words, the present invention makes it possible to automatically carry out asphaltene determination on a large number of samples in a reduced time per sample with high precision without requiring much labor.

What is claimed is:

1. A method for determining an asphaltene content in a heavy hydrocarbon oil, which comprises measuring absorbances of a sample solution having dispersed therein asphaltene particles which is prepared from a sample oil to be determined at two wavelengths selected from a visible light region of from 500 to 1,000 nm, inserting the measured values into a relationship between known asphaltene contents and absorbances at two wavelengths, and performing an operation.

2. A method for determining an asphaltene content in a heavy hydrocarbon oil as in claim 1, wherein the sample solution is prepared by adding an aromatic hydrocarbon to a sample oil to dissolve in each other, adding a warm aliphatic hydrocarbon to the solution to precipitate asphaltene particles, and cooling the solution or allowing the solution to cool.

3. A method for determining an asphaltene content in a heavy hydrocarbon oil as in claims 1 or 2, wherein the two wavelengths selected for absorbance measurement are at least 50 nm apart.

4. A device for determining an asphaltene content in a heavy hydrocarbon oil, which comprises a dip probe or flow cell for sampling a sample solution having dispersed therein asphaltene particles which is prepared from a sample oil to be determined, said dip probe or flow cell being set so as to face with the sample solution and being movable with up-and-down strokes so as to be in contact with or apart from the sample solution, a two-wavelength absorbance detector including a light source, passages for light to allow the light from the light source to pass through a sample solution of a given thickness introduced in the dip probe or flow cell, two interference filters each capable of transmitting the light having transmitted through the sample solution having a different wavelength selected from a range of from 500 to 1,000 nm, and phototubes or photocells each capable of converting the intensity of each of incident light and transmitted light having two different wavelengths into an electrical current, and a computing means capable of converting the electrical current values into an asphaltene content.

5. A device for determining an asphaltene content in a heavy hydrocarbon oil as in claim 4, wherein the two wavelengths selected for absorbance measurement are at least 50 nm apart.

6. A device for determining an asphaltene content in a heavy hydrocarbon oil as in claims 4, wherein the dip probe or flow cell is provided with a washing means for removing the sample solution for determination attached to or remained on the dip probe or flow cell by passing a washing solution every time absorbances of the sample are determined.

7. A device for determining an asphaltene content in a heavy hydrocarbon oil as in claims 4, wherein said device further includes a means for controlling the washing means, every time the determination of one sample is completed, provided to the dip probe or flow cell with the successive determination of each absorbances of the sample contained the sample containers by moving with the dip probe or flow cell.

* * * * *